United States Patent [19]

Mason et al.

[11] 4,217,283

[45] Aug. 12, 1980

[54] 3-AZABICYCLO(3.1.0)HEXAN-4-ONE-2-CARBONITRILE

[75] Inventors: Ronald F. Mason, Westwell, Nr. Ashford; Barry R. J. Devlin, Sittingbourne, both of England

[73] Assignee: Shell Oil Company, Houston, Tex.

[21] Appl. No.: 14,528

[22] Filed: Feb. 23, 1979

[30] Foreign Application Priority Data

Mar. 1, 1978 [GB] United Kingdom ................ 8066/78

[51] Int. Cl.$^2$ .......................................... C07D 207/44
[52] U.S. Cl. .............................................. 260/326.5 B
[58] Field of Search ................................. 260/326.5 B

[56] References Cited

PUBLICATIONS

Kerr, Michael William, Chemical Abstracts, vol. 87, 17,311w (1977).
Achini, Roland et al., Chemical Abstracts, vol. 87, 84811x, (1977).

*Primary Examiner*—Jose Tovar

[57] ABSTRACT

3-Azabicyclo(3.1.0)hexan-4-one-2-carbonitriles, and a method for their synthesis.

1 Claim, No Drawings

3-AZABICYCLO(3.1.0)HEXAN-4-ONE-2-CARBONITRILE

BACKGROUND OF THE INVENTION

3-Azabicyclo(3.1.0)hexane-2-carboxylic acid and certain of its congeners have been found to be plant male gametocides: U.S. Pat. No. 4,047,930 (the compounds are designated therein as 2-carboxy-3,4-methanopyrrolidines).

DESCRIPTION OF THE INVENTION

It has been found that 3-azabicyclo(3.1.0)hexane-2-carboxylic acid can be prepared by:

(1) reducing 3-azabicyclo(3.1.0)hexan-4-one-2-carbonitrile to form 3-azabicyclo(3.1.0)hexane-2-carbonitrile;

(2) converting 3-azabicyclo(3.1.0)hexane-2-carbonitrile to 3-azabicyclo(3.1.0)hexane-2-carboxylic acid:
  (a) by treating the nitrile with barium hydroxide to form the barium salt of the acid, then treating the salt with sulfuric acid;
  (b) by treating the nitrile with hydrochloric acid.

This invention is the novel 3-azabicyclo(3.1.0)hexan-4-one-2-carbonitrile intermediate, and a method for its preparation.

This novel intermediate is described by the formula:

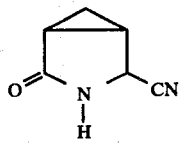

According to the method of this invention, it is prepared by treating a cyclopropyl derivative of the formula

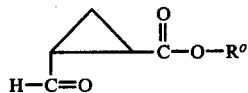

wherein $R^o$ is an alkali metal, alkaline earth metal, ammonium- or alkyl-substituted ammonium ion, or optionally substituted alkyl, and the formyl group has a cis-relationship with the —COOR$^o$ group, with a cyanide in the presence of a compound of the general formula $$RNH_2 \qquad (III)$$

wherein R has the meaning defined above.

In these compounds, each alkyl and alkenyl moiety suitably is straight-chain or branched-chain in configuration.

Preferred precursor cyclopropyl derivatives are those wherein $R^o$ is an alkali metal ion, the ammonium ion, or alkyl from 1 to 6 carbon atoms, e.g., methyl or ethyl.

Suitable cyanides include, for example, hydrogen cyanide, cyanide-containing salts as well as compounds which can generate hydrogen cyanide. Examples of cyanide containing salts are alkali cyanides such as sodium or potassium cyanide as well as ammonium cyanide or alkyl substituted ammonium cyanides such as tri- or tetramethyl ammonium cyanide. Examples of compounds which can generate hydrogen cyanide are aldehyde and ketone cyanohydrins such as acetone cyanohydrin, methyl ethyl ketone cyanohydrin and acetaldehyde cyanohydrin.

Conveniently hydrogen cyanide is added to a cooled solution of the cyclopropyl derivative. When using a cyanide-containing salt, such as sodium or potassium cyanide, the treatment is conveniently carried out in the additional presence of an ammonium halide, such as ammonium chloride or bromide, which will enhance the formation of ammonium cyanide in the reaction mixture. Good results are obtained as a rule when the cyanide is used in a slight molar excess, e.g., 3–10%, in particular 4–7%, based on the cyclopropyl derivative.

The compound of Formula III is either ammonia or a primary amine. Suitable primary amines are alkyl amines, the alkyl group of which contain from 1 to 6 carbon atoms and which may be substituted with one or more halogen atoms or alkoxy groups; cycloalkyl amines, and benzyl amines which may contain up to 3 inert substituents on the phenyl ring. Examples of primary amines include methylamine, ethylamine, isopropylamine, cyclohexylamine and benzylamine. Preference is given to the use of ammonia (R=H).

Ammonia may be present in the solution containing the cyclopropyl derivative prior to addition of the cyanide, but it can also be added to a mixture already containing a cyanide, which may be in the form of liquid hydrogen cyanide or as a cyanide-containing salt or as a compound which can generate a cyanide. Best results are obtained by saturating a cooled solution of the cyclopropyl derivative and liquid hydrogen cyanide with ammonia. It is advantageous to add ammonia slowly and continuously during the course of the reaction.

The addition of the cyanide and/or the compound of Formula III to the solution of the cyclopropyl derivative is preferably carried out at relatively low temperatures, i.e., at a temperature below 15° C., preferably below 5° C., in order to optimise the uptake of the reactant concerned. When the reactants have been put together an exothermic reaction will normally occur, sometimes after allowing the reaction mixture to reach ambient temperature. The reaction is normally completed by heating the reaction mixture at a temperature up to 80° C., preferably under reflux conditions.

A small amount of a base such as an amine, preferably a tertiary amine having up to 10 carbon atoms, e.g., triethylamine or triethanolamine, or a secondary amine having up to 10 carbon atoms, e.g., piperidine or diethylamine, may also be included in the reaction mixture, as it has a catalytic effect on the reaction. The amount of the base applied generally lies in the range 0.3–10%, preferably 2–6% based on the weight of the cyclopropyl derivative employed.

The process of the invention can be carried out conveniently in a solvent. Suitable solvents comprise aliphatic alcohols, such as methanol, ethanol, isopropyl alcohol, 2-chloro-ethanol and ethylene glycol, ethers such as tetrahydrofuran, or aliphatic nitriles such as acetonitrile. Very good results have been obtained with ethanol as the solvent. Mixtures of two or more solvents and/or of inert diluents can also be used. It is also possible to use an excess of ammonia or hydrogen cyanide as a solvent or co-solvent.

The process is normally carried out at atmospheric pressure. If required, superatmospheric pressures, e.g., up to 10 atmospheres may be employed, however.

The product of the process usually is a mixture of the cis-and trans-isomers, which isomers each consist of the optical isomers. For preparing 3-azabicyclo(3.1.0)hexane-2-carbonitrile, the cis/trans isomer mixtures, or the individual isomers can be used. The individual isomers can be isolated from the appropriate mixtures by fractional crystallization techniques, e.g., by preferential crystallization from ethanol or by fractional chromatographic techniques such as thin layer or column chromatography, using the appropriate carriers and eluent(s).

The cyclopropyl derivatives which are the starting materials can be conveniently prepared by methods known in the art. A suitable method comprises for instance the reaction of an olefinic compound and a sulphur ylid as described in U.S. Pat. No. 3,397,233. Thus, ethyl 2-formylcyclopropanecarboxylate can be prepared by adding acrolein to a solution of ethyl(dimethylsulfuranylidene)acetate in acetone.

Preparation of 3-azabicyclo(3.1.0)hexan-4-one-2-carbonitrile by means of the process of the invention in particular instances, and its conversion 3-azabicyclo(3.1.0)hexane-2-carbonitrile, and it to 3-azabicyclo(3.1.0)hexane-2-carboxylic acid, is demonstrated in the following examples.

EXAMPLE 1

A mixture of 21.3 g of cis ethyl 2-formylcyclopropanecarboxylate, 50 ml of absolute ethanol and 4 drops of piperidine was cooled to 0° C. 6 ml (4.2g) of hydrogen cyanide was added, the mixture was saturated with anhydrous ammonia, and the resulting mixture was allowed to warm to room temperature. After the addition of further ammonia the temperature rose slowly and the mixture was kept at 70°–75° C. for 45 minutes. After removal of the volatile components in a film evaporator under reduced pressure, the remaining mixture was saturated with ethanol under cooling in an ice bath, then filtered and recrystallized from 30 ml ethanol to give a solid, mp 135°–136° C. The product was characterized by elemental analysis, and by proton and $C^{13}$ magnetic resonance spectroscopy as pure cis 3-azabicyclo(3.1.0)hexan-4-one-2-carbonitrile.

A further amount of that compound, as a mixture of cis and trans isomers, was obtained by chromatographing the mother liquor over silica gel, using methylene dichloride as eluent. An analytically pure sample of the trans isomer, mp 89°–90° C., was obtained using liquid-liquid chromatography. The compound was characterized by nuclear magnetic spectroscopy.

Similar results were obtained when the reaction was carried out using 95.85 g of cis ethyl 2-formylcyclopropanecarboxylate as starting material. (66% of cis/-trans product was isolated).

EXAMPLE 2

22.2 g of ammonium chloride and 20.0 g of sodium cyanide were mixed and dissolved in 175 ml of ammonia (specific gravity: 0.880). 75 ml of ethanol was added. The resulting solution was saturated with ammonia at 0°–5° C. 26.7 g of cis ethyl 2-formylcyclopropanecarboxylate was added over a five-minute period. The mixture was heated to and held at 25° C. for 5 hours. The volatile materials therein were removed in a film evaporator at 60° C. The residue was extracted with 150 ml of boiling ethanol and filtered. The solvent was evaporated from the filtrate, the residue was taken up in 30 ml of hot ethanol, and the solution was cooled to give pure cis 3-azabicyclo(3.1.0)hexan-4-one-2-carbonitrile, mp: 135°–137° C. A mixture of the cis and trans isomers was obtained by treating the mother liquor by procedures described in Example 1, a mixture of ethanol and methylene dichloride being used as the eluent.

EXAMPLE 3

18 g of a mixture of 45% cis and 55% trans 3-azabicyclo(3.1.0)hexan-4-one-2-carbonitrile was mixed with 250 ml of dry methylene chloride. The mixture was stirred and 32 g of triethyloxonium tetrafluoroborate was added in portions. Cooling was not required. Upon stirring for 30 minutes, a heavy oil began to separate. The mixture then was stirred for 15 hours at room temperature. The volatile materials were evaporated under reduced pressure. The residue, a yellow oil, was dissolved in 120 ml of dry ethanol. The solution was stirred and cooled to 0° C. and 12.8 g of sodium borohydride was added, in portions. The mixture was stirred overnight, the solvent was evaporated and the residue was treated with 100 ml of water. The resulting mixture was extracted with ether. The ether was evaporated from the extract to leave a viscous yellow oil. The oil was dissolved in benzene, the solution was dried (MgSO$_4$) and the benzene was evaporated. The residue was distilled under reduced pressure to give a product, bp: 56°–60° C., 0.3 Torr, which NMR spectroscopy carried out in hexadeuterobenzene established to contain 91% of the trans isomer and 8% of the cis isomer of 3-azabicyclo(3.1.0)hexane-2-carbonitrile.

7.0 g of the product was treated with a cold isopropyl alcohol/petroleum ether mixture from which the trans isomer crystallized in the form of white needles, mp 39°–40° C.

EXAMPLE 4

10 g of cis 3-azabicyclo(3.1.0)hexan-4-one-2-carbonitrile was dissolved in 50 ml of dry methylene chloride, and 19 g of triethyloxonium tetrafluoroborate was added to the stirred solution at 10°–15° C. The resulting mixture was stirred for 18 hours, then the volatile materials were evaporated under reduced pressure. The residue was dissolved in dry ethanol; the solution was cooled to 5°–10° C. and 4.0 g of sodium borohydride was added in portions thereto over a ten-minute period. The resulting mixture was stirred for 20 hours at room temperature. The volatile materials were evaporated. 150 ml of water was added to the residue and the resulting solution was extracted with ether. The extract was dried (MgSO$_4$) and the solvent was evaporated. The residue, crude 3-azabicyclo(3.1.0)hexane-2-carbonitrile, was dissolved in 80 ml of 6N hydrochloric acid and the solution was refluxed for four hours. The water was evaporated until the volume of the mixture was 20 ml, when it was poured down a column of Dowex W-X8 and washed free of chloride ions. The product was eluted with 2N ammonium hydroxide, collecting a total volume of 3 liters. Evaporation of the volatile materials gave a syrup. 100 ml of ethanol was added; the mixture was heated and filtered. Evaporation of the volatile materials gave a pale yellow oil which solidified at 1 Torr. pressure. The NMR and IR spectra of that product were identical to the naturally-occurring cis 3-azabicyclo(3.1.0)hexane-2-carboxylic acid, the cis content of the product being greater than 90%.

In a similar experiment, starting from 4.5 g cis 3-azabicyclo(3.1.0)hexan-4-one-2-carbonitrile, a semisolid residue was obtained, to which benzene was added. Evaporation of the benzene left a yellow oil which gave, on distillation, cis 3-azabicyclo(3.1.0)hexane-2-carboxylic acid, as a liquid, bp 80°–86° C. at 1 Torr. pressure.

EXAMPLE 5

34.6 g of a mixture of the cis and trans isomers of 3-azabicyclo(3.1.0)hexane-2-carbonitrile, 102.8 g of barium hydroxide octahydrate, and 500 ml of water was refluxed for 7 hours. The mixture was cooled, and then was carefully neutralized to pH 6 with 33.2 g of 96% sulfuric acid in 500 ml of water. Celite was added and the mixture was filtered. The solvent was evaporated and the residue was extracted with hot ethanol. The undissolved solid was an approximately 2/1 mixture of trans and cis 3-azabicyclo(3.1.0)hexane-2-carboxylic acid. The solid obtained from evaporation of the solvent from the extract was an approximately 2.2/1 mixture of the cis and trans isomers.

The solid was subjected to chromatography on a cation exchange resin, using 1.5N hydrochloric acid as eluent, to give the cis isomer as a solid, mp 226°–228° C. (with gas evolution), as the more mobile isomer. The less mobile isomer was the trans isomer, mp 202°–206° C. (with gas evolution).

We claim:
1. 3-azabicyclo(3.1.0)-hexan-4-one-2-carbonitrile.

* * * * *